(12) United States Patent
Mochizuki et al.

(10) Patent No.: US 11,226,476 B2
(45) Date of Patent: Jan. 18, 2022

(54) SPECIMEN OBSERVATION APPARATUS

(71) Applicant: OLYMPUS CORPORATION, Hachioji (JP)

(72) Inventors: Tsuyoshi Mochizuki, Tokyo (JP); Shintaro Takahashi, Tokyo (JP); Akira Matsushita, Tokyo (JP); Yohei Tanikawa, Tokyo (JP); Masaru Mizunaka, Tokyo (JP); Shinichi Takimoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 290 days.

(21) Appl. No.: 16/366,682

(22) Filed: Mar. 27, 2019

(65) Prior Publication Data

US 2019/0219809 A1   Jul. 18, 2019

Related U.S. Application Data

(63) Continuation of application No. PCT/JP2017/034826, filed on Sep. 27, 2017.

(30) Foreign Application Priority Data

Sep. 30, 2016  (JP) .............................. JP2016-192478

(51) Int. Cl.
*G02B 21/34* (2006.01)
*G02B 21/08* (2006.01)
(Continued)

(52) U.S. Cl.
CPC ............ *G02B 21/086* (2013.01); *C12M 1/34* (2013.01); *G01N 21/01* (2013.01); *G01N 21/17* (2013.01);
(Continued)

(58) Field of Classification Search
CPC .. G02B 21/00; G02B 21/002; G02B 21/0016; G02B 21/025; G02B 21/06;
(Continued)

(56) References Cited

U.S. PATENT DOCUMENTS 4,621,911 A   11/1986   Lanni et al.
4,969,037 A   11/1990   Poleschinski et al.
(Continued)

FOREIGN PATENT DOCUMENTS

CN   105264358 A   1/2016
EP   1553166 A1   7/2005
(Continued)

OTHER PUBLICATIONS

International Search Report (ISR) dated Jan. 9, 2018 issued in International Application No. PCT/JP2017/034826.
(Continued)

*Primary Examiner* — Mustak Choudhury
(74) *Attorney, Agent, or Firm* — Holtz, Holtz & Volek PC

(57) ABSTRACT

An observation apparatus including: a top plate on which a container in which a specimen is accommodated can be placed, and through which illumination light can pass; a light source that emits the illumination light upward from below the specimen; an objective lens that focuses, below the specimen and the top plate, transmitted light which is the illumination light that has passed through the specimen from thereabove and that has passed through the top plate; and a camera that captures the transmitted light,
wherein the light source emits the illumination light toward an area above the specimen from outside the objective lens in a radial direction, and the top plate is provided with a mark that specifies a viewing-field area of the camera.

23 Claims, 13 Drawing Sheets

(51) Int. Cl.
*G02B 21/26* (2006.01)
*G02B 21/36* (2006.01)
*G01N 21/59* (2006.01)
*G01N 21/01* (2006.01)
*G02B 21/33* (2006.01)
*G01N 21/17* (2006.01)
*C12M 1/34* (2006.01)

(52) U.S. Cl.
CPC ........... *G01N 21/59* (2013.01); *G02B 21/088* (2013.01); *G02B 21/26* (2013.01); *G02B 21/33* (2013.01); *G02B 21/34* (2013.01); *G02B 21/36* (2013.01); *G01N 2201/062* (2013.01)

(58) Field of Classification Search
CPC .. G02B 21/082; G02B 21/084; G02B 21/086; G02B 21/088; G02B 21/26; G02B 21/33; G02B 21/34; G02B 21/36; G02B 21/248; G02B 21/361; G02B 21/362; G02B 21/367; G02B 21/368; G01N 15/1012; G01N 15/1429; G01N 15/1436; G01N 21/01; G01N 21/17; G01N 21/59; G01N 21/6456; G01N 2201/062; C12M 1/34; A61B 5/0059
See application file for complete search history.

(56) References Cited

U.S. PATENT DOCUMENTS

| | | |
|---|---|---|
| 5,038,258 A | 8/1991 | Koch et al. |
| 5,751,475 A | 5/1998 | Ishiwata et al. |
| 6,025,956 A | 2/2000 | Nagano et al. |
| 6,643,061 B2 | 11/2003 | Osa et al. |
| 8,699,128 B2 | 4/2014 | Yamashita et al. |
| 8,873,027 B2 | 10/2014 | Sugiyama et al. |
| 8,947,519 B2 | 2/2015 | Tsujimoto et al. |
| 9,766,445 B2 | 9/2017 | Kei et al. |
| 10,281,704 B2 | 5/2019 | Takahashi et al. |
| 10,877,256 B2 | 12/2020 | Hirata et al. |
| 10,914,931 B2 | 2/2021 | Hirata et al. |
| 2001/0028497 A1 | 10/2001 | Uhl |
| 2004/0113043 A1 | 6/2004 | Ishikawa et al. |
| 2005/0105172 A1 | 5/2005 | Hasegawa et al. |
| 2006/0072190 A1* | 4/2006 | Okugawa ........... G02B 21/0088 359/368 |
| 2007/0177255 A1 | 8/2007 | Kanegasaki et al. |
| 2008/0201083 A1 | 8/2008 | Hata et al. |
| 2008/0291534 A1 | 11/2008 | Okugawa |
| 2009/0051901 A1 | 2/2009 | Shen et al. |
| 2010/0208053 A1 | 8/2010 | Hasegawa et al. |
| 2011/0089339 A1 | 4/2011 | Yamashita et al. |
| 2013/0033744 A1* | 2/2013 | Folling ................. G02B 21/26 359/392 |
| 2013/0130307 A1 | 5/2013 | Sugiyama et al. |
| 2013/0156287 A1 | 6/2013 | Houjou et al. |
| 2013/0229707 A1 | 9/2013 | Sakaguchi |
| 2014/0015954 A1 | 1/2014 | Tsujimoto et al. |
| 2014/0030737 A1 | 1/2014 | Holmes et al. |
| 2014/0038206 A1 | 2/2014 | Holmes et al. |
| 2014/0126049 A1 | 5/2014 | Yamamoto |
| 2014/0193892 A1 | 7/2014 | Mohan et al. |
| 2014/0273188 A1* | 9/2014 | Mohan ................... G02B 21/00 435/287.2 |
| 2014/0333997 A1 | 11/2014 | Oda |
| 2014/0340476 A1 | 11/2014 | Sun et al. |
| 2015/0031051 A1 | 1/2015 | Mohan et al. |
| 2015/0131142 A1 | 5/2015 | Matsumoto et al. |
| 2015/0204788 A1 | 7/2015 | Pangarkar et al. |
| 2015/0253561 A1 | 9/2015 | Lee et al. |
| 2015/0264235 A1 | 9/2015 | Houjou et al. |
| 2015/0362716 A1 | 12/2015 | Kei et al. |
| 2016/0048011 A1 | 2/2016 | Suzuki et al. |
| 2016/0249810 A1 | 9/2016 | Darty et al. |
| 2017/0023478 A1 | 1/2017 | Holmes et al. |
| 2017/0115289 A1 | 4/2017 | Holmes et al. |
| 2017/0146447 A1 | 5/2017 | Mohan et al. |
| 2017/0261732 A1* | 9/2017 | Takahashi ............ G02B 21/06 |
| 2017/0355949 A1* | 12/2017 | Hirata .................. C12M 41/36 |
| 2018/0252648 A1 | 9/2018 | Dohi |
| 2018/0267285 A1 | 9/2018 | Hirata et al. |
| 2018/0329193 A1 | 11/2018 | Hirata et al. |
| 2019/0218500 A1 | 7/2019 | Takimoto et al. |
| 2019/0219808 A1 | 7/2019 | Takahashi et al. |
| 2019/0219810 A1 | 7/2019 | Mizunaka et al. |
| 2019/0339271 A1 | 11/2019 | Mohan et al. |
| 2020/0088985 A1 | 3/2020 | Hirata |
| 2020/0103406 A1 | 4/2020 | Holmes et al. |
| 2020/0318058 A1 | 10/2020 | Mochizuki et al. |

FOREIGN PATENT DOCUMENTS

| | | |
|---|---|---|
| EP | 1615061 A1 | 1/2006 |
| EP | 1630586 A1 | 3/2006 |
| EP | 2312367 A1 | 4/2011 |
| EP | 2562245 A1 | 2/2013 |
| EP | 2955502 A1 | 12/2015 |
| EP | 3211469 A1 | 8/2017 |
| EP | 3279713 A1 | 2/2018 |
| EP | 3521410 A1 | 8/2019 |
| GB | 2512793 A | 10/2014 |
| JP | S57178212 A | 11/1982 |
| JP | H02232614 A | 9/1990 |
| JP | H02272412 A | 11/1990 |
| JP | H06217989 A | 8/1994 |
| JP | H07261089 A | 10/1995 |
| JP | H09179034 A | 7/1997 |
| JP | 2000327483 A | 11/2000 |
| JP | 2001025387 A | 1/2001 |
| JP | 2001166219 A | 6/2001 |
| JP | 2003021628 A | 1/2003 |
| JP | 2004070276 A | 3/2004 |
| JP | 2004318185 A | 11/2004 |
| JP | 2004348104 A | 12/2004 |
| JP | 2004361485 A | 12/2004 |
| JP | 2005010258 A | 1/2005 |
| JP | 3684106 A | 6/2005 |
| JP | 2005326495 A | 11/2005 |
| JP | 2005331623 A | 12/2005 |
| JP | 2006030583 A | 2/2006 |
| JP | 2006174764 A | 7/2006 |
| JP | 2006179387 A | 7/2006 |
| JP | 2007264410 A | 10/2007 |
| JP | 2007323094 A | 12/2007 |
| JP | 2008092882 A | 4/2008 |
| JP | 2008209726 A | 9/2008 |
| JP | 2009106305 A | 5/2009 |
| JP | 2009109566 A | 5/2009 |
| JP | 2009217222 A | 9/2009 |
| JP | 2010085705 A | 4/2010 |
| JP | 2011008188 A | 1/2011 |
| JP | 2011101617 A | 5/2011 |
| JP | 2011102970 A | 5/2011 |
| JP | 2011141444 A | 7/2011 |
| JP | 2013521522 A | 6/2013 |
| JP | 2013152454 A | 8/2013 |
| JP | 2013238797 A | 11/2013 |
| JP | 2015084059 A | 4/2015 |
| JP | 2016000007 A | 1/2016 |
| JP | 6066110 B2 | 1/2017 |
| JP | 2018072845 A | 5/2018 |
| KR | 100813915 B1 | 3/2008 |
| WO | 2004109361 A1 | 12/2004 |
| WO | 2006101056 A1 | 9/2006 |
| WO | 2011115189 A1 | 9/2011 |
| WO | 2011132586 A1 | 10/2011 |
| WO | 2012029817 A1 | 3/2012 |
| WO | 2013047315 A1 | 4/2013 |
| WO | 2013100025 A1 | 7/2013 |
| WO | 2013157606 A1 | 10/2013 |
| WO | 2014018805 A2 | 1/2014 |
| WO | 2014038871 A1 | 3/2014 |

(56) References Cited

FOREIGN PATENT DOCUMENTS

| WO | 2014041820 A1 | 3/2014 |
|---|---|---|
| WO | 2014127372 A2 | 8/2014 |
| WO | 2016158780 A1 | 10/2016 |
| WO | 2016158782 A1 | 10/2016 |
| WO | 2018061951 A1 | 4/2018 |

OTHER PUBLICATIONS

Written Opinion dated Jan. 9, 2018 issued in International Application No. PCT/JP2017/034826.
Webb, "Condenser-free contrast methods for transmitted-light microscopy", Journal of Microscopy published by John Wiley & Sons, Ltd, vol. 257, Issue 1, pp. 8-22.
Chinese Office Action (and English language translation thereof) dated Dec. 27, 2019 issued in Chinese Application No. 201580085163.7.
Extended European Search Report (EESR) dated Dec. 19, 2017 issued in European Application No. 16772661.1.
Extended European Search Report (EESR) dated Mar. 12, 2020 issued in European Application No. 17855906.8.
Extended European Search Report (EESR) dated Oct. 29, 2018 issued in European Application No. 16772663.7.
International Search Report (ISR) (and English translation thereof) dated Aug. 29, 2017 issued in International Application No. PCT/JP2017/019895.
International Search Report (ISR) (and English translation thereof) dated Mar. 8, 2016 issued in International Application No. PCT/JP2015/084805.
International Search Report (ISR) and Written Opinion dated Dec. 26, 2017 issued in International Application No. PCT/JP2017/033979.
International Search Report (ISR) and Written Opinion dated Jun. 21, 2016 issued in International Application No. PCT/JP2016/059686.
International Search Report (ISR) and Written Opinion dated Jun. 28, 2016 issued in International Application No. PCT/JP2016/059694.
International Search Report (ISR) and Written Opinion dated Mar. 22, 2016 issued in International Application No. PCT/JP2015/085479.
International Search Report (ISR) dated Dec. 19, 2017 issued in International Application No. PCT/JP2017/033820.
Japanese Office Action (and English language translation thereof) dated Feb. 9, 2021 issued in Japanese Application No. 2019-521536.
Japanese Office Action dated Dec. 3, 2019 (and English translation thereof) issued in Japanese Patent Application No. 2017-225493.
Office Action (Ex Parte Quayle) dated Apr. 22, 2021 issued in related U.S. Appl. No. 16/364,946.
Office Action (Non-Final Rejection) dated Apr. 6, 2020 issued in related U.S. Appl. No. 15/984,949.
Office Action (Non-Final Rejection) dated Feb. 21, 2019 issued in related U.S. Appl. No. 15/690,024.
Office Action (Non-Final Rejection) dated Jun. 2, 2021 issued in related U.S. Appl. No. 16/360,205.
Office Action (Non-Final Rejection) dated May 18, 2020 issued in related U.S. Appl. No. 16/003,402.
Office Action (Non-Final Rejection) dated Sep. 7, 2018 issued in U.S. Appl. No. 15/607,666.
Related U.S. Appl. No. 16/003,402; First Named Inventor Tadashi Hirata; Title: "Observation Device"; filed Jun. 8, 2018.
Related U.S. Appl. No. 16/689,671; First Named Inventor Tadashi Hirata; Title: "Observation Device"; filed Nov. 20, 2019.
Related U.S. Appl. No. 15/607,666, First Named Inventor: Shintaro Takahashi, Title: "Observation Apparatus and Observation Method To Observe a Sample With Reflected Light Transmitted Through the Sample", filed May 29, 2017.
Related U.S. Appl. No. 15/690,024, First Named Inventor Tadashi Hirata, Title: "Observation Apparatus", filed Aug. 29, 2017.
Related U.S. Appl. No. 15/984,949, First Named Inventor Tadashi Hirata, Title: "Observation Device", filed May 21, 2018.
Related U.S. Appl. No. 16/364,946, First Named Inventor Masaru Mizunaka, Title: "Observation Apparatus", filed Mar. 26, 2019.
Written Opinion (and English language translation thereof) dated Aug. 29, 2017 issued in International Application No. PCT/JP2017/019895.
Written Opinion (and English language translation thereof) dated Mar. 8, 2016 issued in International Application No. PCT/JP2015/084805.
Written Opinion dated Dec. 19, 2017 issued in International Application No. PCT/JP2017/033820.
Ford, et al., "Phase-gradient microscopy in thick tissue with oblique back-illumination", Nature Methods, vol. 9, No. 12, pp. 1195-1197, ISSN: 1548-7091.
Ra, et al., "Phase contrast DIC illumination for AFM hybrids", Ultramicroscopy, ELSEVIEr, Amsterdam, NL, vol. 104, No. 3-4, pp. 255-260, ISSN: 0304-3991.
Webb, et al., "Condenser-free contrast methods for transmitted-light microscopy: Condenser-free contrast methods", Journal of Microscopy, vol. 257, No. 1, pp. 8-22, ISSN: 0022-2720.
Japanese Office Action dated Jun. 29, 2021 issued in Japanese Application No. 2018-542613.
Related U.S. Appl. No. 16/360,205, First Named Inventor: Shinichi Takimoto; Title: "Culture Observation System"; filed Mar. 21, 2019.
Notice of Allowance dated Jan. 9, 2019 issued in related U.S. Appl. No. 15/607,666.
Notice of Allowance dated Jun. 9, 2021 issued in related U.S. Appl. No. 16/364,946.
Notice of Allowance dated Nov. 16, 2020 issued in related U.S. Appl. No. 16/003,402.
Notice of Allowance dated Nov. 3, 2020 issued in related U.S. Appl. No. 15/984,949.
Office Action (Final Rejection) dated Jun. 24, 2019 issued in related U.S. Appl. No. 15/690,024.
Office Action (Final Rejection) dated Sep. 9, 2020 issued in related U.S. Appl. No. 16/003,402.
Office Action (Non-Final Rejection) dated Jul. 28, 2020 issued in related U.S. Appl. No. 15/984,949.
U.S. Appl. No. 16/003,402, filed Jun. 8, 2018 and issued as U.S. Pat. No. 10,914,931 on Feb. 9, 2021.
U.S. Appl. No. 16/689,671, filed Nov. 20, 2019.
U.S. Appl. No. 15/607,666, filed May 29, 2017 and issued as U.S. Pat. No. 10,281,704 on May 7, 2019.
U.S. Appl. No. 15/690,024, filed Aug. 29, 2017, now abandoned.
U.S. Appl. No. 15/984,949, filed May 21, 2018 and issued as U.S. Pat. No. 10,877,256 on Dec. 29, 2020.
U.S. Appl. No. 16/364,946, filed Mar. 26, 2019.
U.S. Appl. No. 16/360,205, filed Mar. 21, 2019.
A Chinese Office Action (and English language translation thereof) dated Dec. 27, 2019 issued in Chinese Application No. 201580085163.7, which is a Chinese counterpart of related U.S. Appl. No. 15/984,949.
An Extended European Search Report (EESR) dated Dec. 19, 2017 issued in European Application No. 16772661.1, which is a European counterpart of related U.S. Appl. No. 15/607,666.
An Extended European Search Report (EESR) dated Mar. 12, 2020 issued in European Application No. 17855906.8, which is a European counterpart of related U.S. Appl. No. 16/360,205.
An Extended European Search Report (EESR) dated Oct. 29, 2018 issued in European Application No. 16772663.7, which is a European counterpart of related U.S. Appl. No. 15/690,024.
An International Search Report (ISR) (and English translation thereof) dated Aug. 29, 2017 issued in International Application. No. PCT/JP2017/019895, which is an International counterpart of related U.S. Appl. No. 16/689,671.
An International Search Report (ISR) (and English translation thereof) dated Mar. 8, 2016 issued in International Application No. PCT/JP2015/084805, which is an International counterpart of related U.S. Appl. No. 16/003,402.

(56) References Cited

OTHER PUBLICATIONS

An International Search Report (ISR) and Written Opinion dated Dec. 26, 2017 issued in International Application No. PCT/JP2017/033979, which is an International counterpart of related U.S. Appl. No. 16/360,205.
An International Search Report (ISR) and Written Opinion dated Jun. 21, 2016 issued in International Application No. PCT/JP2016/059686, which is an International counterpart of related U.S. Appl. No. 15/607,666.
An International Search Report (ISR) and Written Opinion dated Jun. 28, 2016 issued in International Application No. PCT/JP2016/059694, which is an International counterpart of related U.S. Appl. No. 15/690,024.
An International Search Report (ISR) and Written Opinion dated Mar. 22, 2016 issued in International Application No. PCT/JP2015/085479, which is an International counterpart of related U.S. Appl. No. 15/984,949.
An International Search Report (ISR) dated Dec. 19, 2017 issued in International Application No. PCT/JP2017/033820, which is an International counterpart of related U.S. Appl. No. 16/364,946.
A Japanese Office Action (and English language translation thereof) dated Feb. 9, 2021 issued in Japanese Application No. 2019-521536, which is a Japanese counterpart of related U.S. Appl. No. 16/689,671.
A Japanese Office Action dated Dec. 3, 2019 (and English translation thereof) issued in Japanese Patent Application No. 2017-225493, which is a Japanese counterpart of related U.S. Appl. No. 15/607,666.
An Office Action (Ex Parte Quayle) dated Apr. 22, 2021 issued in related U.S. Appl. No. 16/364,946.
An Office Action (Non-Final Rejection) dated Apr. 6, 2020 issued in related U.S. Appl. No. 15/984,949.
An Office Action (Non-Final Rejection) dated Feb. 21, 2019 issued in related U.S. Appl. No. 15/690,024.
An Office Action (Non-Final Rejection) dated Jun. 2, 2021 issued in related U.S. Appl. No. 16/360,205.
An Office Action (Non-Final Rejection) dated May 18, 2020 issued in related U.S. Appl. No. 16/003,402.
An Office Action (Non-Final Rejection) dated Sep. 7, 2018 issued in related U.S. Appl. No. 15/607,666.
An Office Action (Final Rejection) dated Jun. 24, 2019 issued in related U.S. Appl. No. 15/690,024.
An Office Action (Final Rejection) dated Sep. 9, 2020 issued in related U.S. Appl. No. 16/003,402.
An Office Action (Non-Final Rejection) dated Jul. 28, 2020 issued in related U.S. Appl. No. 15/984,949.
A Notice of Allowance dated Jan. 9, 2019 issued in related U.S. Appl. No. 15/607,666.
A Notice of Allowance dated Jun. 9, 2021 issued in related U.S. Appl. No. 16/364,946.
A Notice of Allowance dated Nov. 16, 2020 issued in related U.S. Appl. No. 16/003,402.
A Notice of Allowance dated Nov. 3, 2020 issued in related U.S. Appl. No. 15/984,949.
A Written Opinion (and English language translation thereof) dated. Aug. 29, 2017 issued in International Application No. PCT/JP2017/019895, which is an International counterpart of related U.S. Appl. No. 16/689,671.
A Written Opinion (and English language translation thereof) dated Mar. 8, 2016 issued in International Application No. PCT/JP2015/084805, which is an International counterpart of related U.S. Appl. No. 16/003,402.
A Written Opinion dated Dec. 19, 2017 issued in International Application No. PCT/JP2017/033820, which is a International counterpart of related U.S. Appl. No. 16/364,946.
3 non-patent literature documents.

* cited by examiner

SPECIMEN OBSERVATION APPARATUS

CROSS-REFERENCE TO RELATED APPLICATIONS

This is a continuation of International Application PCT/JP2017/034826, with an international filing date of Sep. 27, 2017, which is hereby incorporated by reference herein in its entirety.

This application is based on Japanese Patent Application No. 2016-192478, the contents of which are incorporated herein by reference.

TECHNICAL FIELD

The present invention relates to an observation apparatus.

BACKGROUND ART

In the related art, there is a known observation apparatus that is for observing a specimen and that is installed in a clean bench (for example, see Patent Literatures 1 and 2).

Incidentally, in the case in which a colony of cells accommodated in a container is collected while visually observing the colony with a microscope, the desired colony is specified by providing a circle (mark) on the back surface of a bottom of the container so as to surround the desired colony and by using this circle as a marker.

CITATION LIST

Patent Literature

{PTL 1} Japanese Unexamined Patent Application, Publication No. 2001-25387
{PTL 2} Japanese Unexamined Patent Application, Publication No. 2009-106305

SUMMARY OF INVENTION

An aspect of the present invention is an observation apparatus including: a top plate on which a container in which a specimen is accommodated can be placed, and through which illumination light can pass; a light-source portion that emits the illumination light upward from below the specimen; an objective lens that focuses, below the specimen and the top plate, transmitted light which is the illumination light that has passed through the specimen from thereabove and that has passed through the top plate; and an image-acquisition portion that captures the transmitted light, wherein the light-source portion emits the illumination light toward an area above the specimen from outside the objective lens in a radial direction, and the top plate is provided with a mark that specifies a viewing-field area of the image-acquisition portion.

DESCRIPTION OF EMBODIMENTS

First Embodiment

An observation apparatus according to a first embodiment of the present invention will be described below with reference to the drawings.

Figure 1:
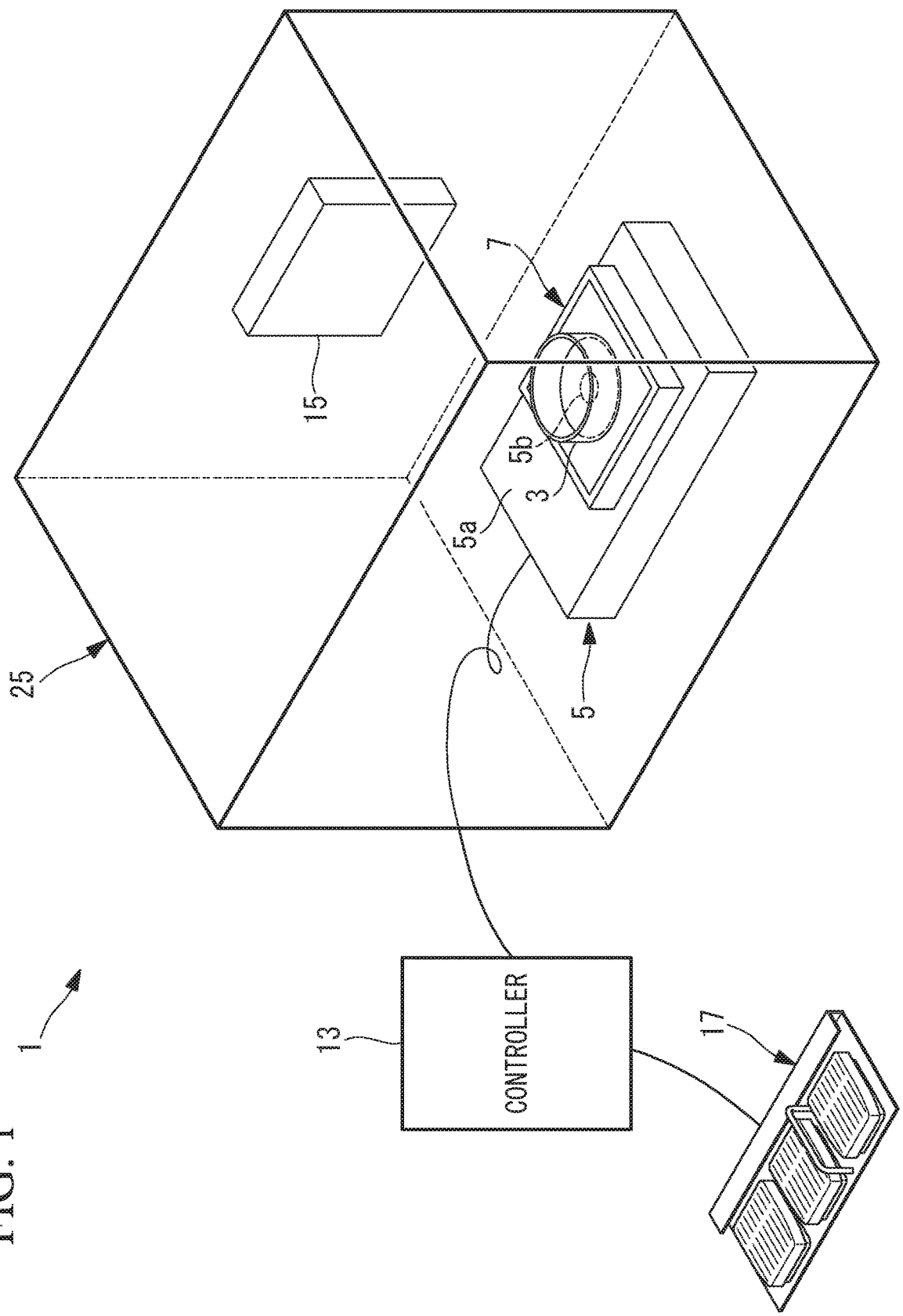
FIG. 1 is a diagram showing, in outline, the configuration of an observation apparatus according to a first embodiment of the present invention.

An observation apparatus 1 according to this embodiment can be used, for example, by being installed in a clean bench 25, as shown in FIG. 1.

Figure 2:
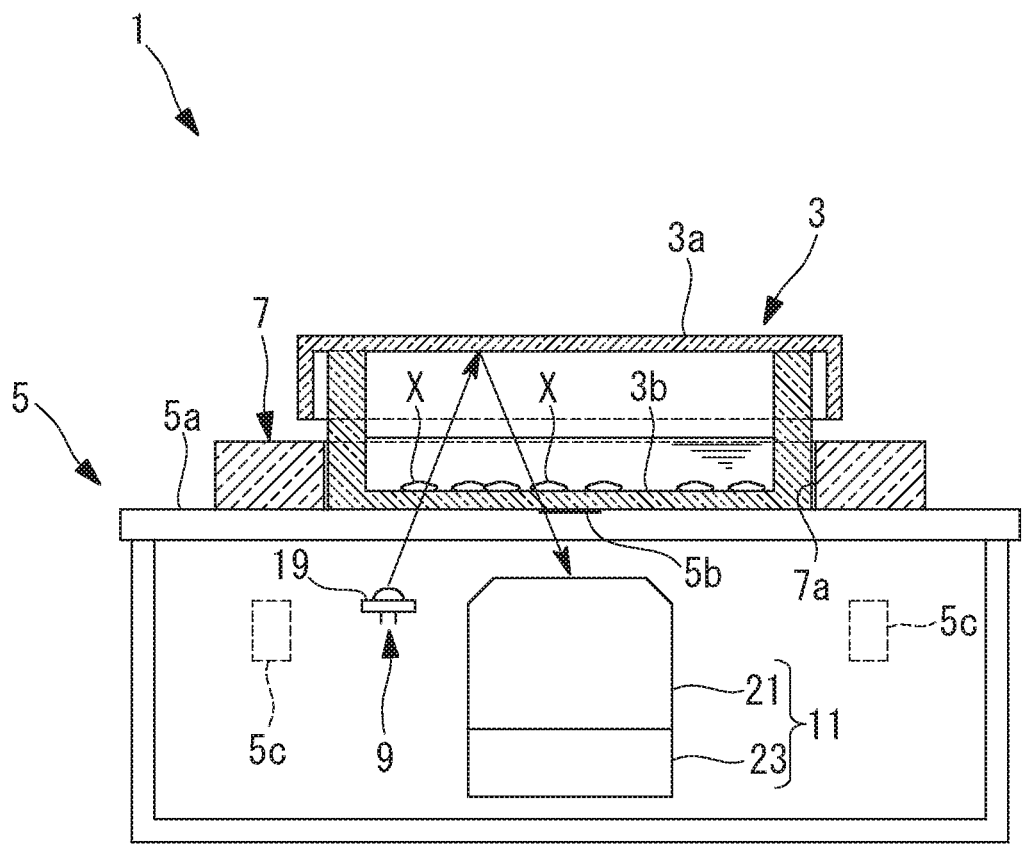
FIG. 2 is a longitudinal cross-sectional diagram of the observation apparatus in FIG. 1.

As shown in FIGS. 1 and 2, the observation apparatus 1 is provided with: a housing 5 that has a top plate 5a on which specimens X accommodated in a container 3 are placed; an adaptor 7 having a through-hole 7a that holds the container 3 placed on the top plate 5a of the housing 5 in a fitted state; a light-source portion 9 and an image-acquisition portion 11 that are accommodated in the housing 5; a controller 13 that controls the light-source portion 9 and the image-acquisition portion 11; a display portion 15 that displays an image acquired by the image-acquisition portion 11; and a foot pedal (operating portion) 17 that allows a user to input an instruction to be sent to the controller 13.

The housing 5 is formed in the form of, for example, a cuboid having outer surfaces in which irregularities thereof are minimized. By having such an external shape, it is possible to facilitate sterilization of the outer surface of the housing 5 by means of wiping with 70% ethanol or the like. The top plate 5a of the housing 5 is made of an optically transparent material, for example, glass, through which illumination light can pass, and is disposed so as to cover the area above the light-source portion 9 and the image-acquisition portion 11.

In addition, the housing 5 is formed of a UV-resistant material, such as a metal, except for the top plate 5a. By using such a material, it is possible to sterilize the housing 5 by means of a UV germicidal lamp in the clean bench. For example, the housing 5 may be formed of a hydrogen-peroxide-gas-resistant material such as stainless steel and alumite. In this case, gaps in the housing 5, such as holes through which wires pass, may be sealed with a hydrogen-peroxide-gas-resistant material such as silicon. By doing so, it is possible to cope with hydrogen-peroxide-gas sterilization.

In addition, the housing 5 is configured so that the top plate 5a is substantially horizontally disposed. By substantially horizontally disposing the top plate 5a, it is possible to use the top plate 5a of the housing 5 as a worktable when not performing observation. The top plate 5a has a mark 5b, such as a circle, on one surface thereof. This mark 5b is disposed in an optical axis of an objective lens 21 of the image-acquisition portion 11, described later, and specifies a viewing-field area of the image-acquisition portion 11.

In addition, the mark 5b may be provided on a front surface or a back surface of the top plate 5a so long as the user can visually recognize the mark 5b. It suffices that the mark 5b has, for example, a size or a shape that allows a colony of cells to be collected as the specimen X to be distinguished from other colonies when the colony of cells to be collected is positioned with respect to the mark 5b, and the mark 5b has, for example, a large enough size to accommodate the colony of cells to be collected therein.

In addition, the housing 5 is provided with an electromagnet (movement restricting portion) 5c that restricts relative movement between the adaptor 7 and the top plate 5a. For example, two electromagnets 5c are disposed outside the through-hole 7a of the adaptor 7 in a radial direction, and are powered on by means of the foot pedal 17.

The container 3 is, for example, a cell-culturing flask having a lid (top-plate portion) 3a and is entirely constituted of an optically transparent resin. Examples of the specimens X include cells in the process of culturing and so forth.

The adaptor 7 is formed, for example, into the form of a substantially rectangular plate that is larger than the container 3, and has the above-described through-hole 7a for fitting the container 3 thereto. This adaptor 7 is capable of securing the container 3 fitted to the through-hole 7a by means of a screw.

In addition, the adaptor 7 is formed of a magnetic body. On the top plate 5a, movements of the adaptor 7 placed on the top plate 5a of the housing 5 are restricted by a magnetic force generated as a result of the electromagnets 5c of the housing 5 being powered on, and the restriction on the movements on the top plate 5a is canceled as a result of the magnetic force being eliminated when the electromagnets 5c are powered off.

The light-source portion 9 is provided with a single LED light source 19 that is disposed facing the top plate 5a with the position thereof being displaced in an intersecting direction with respect to an optical axis of the image-acquisition portion 11. The LED light source 19 emits illumination light diagonally upward, causing the illumination light to pass through the top plate 5a and a bottom surface 3b of the container 3, and subsequently causes the illumination light to be reflected at a lid 3a of the container 3, thereby radiating the illumination light onto the specimens X in the container 3 from diagonally thereabove.

The image-acquisition portion 11 is provided with the above-described objective lens 21 that is disposed below the top plate 5a facing the top plate 5a and a camera 23 that captures light focused by the objective lens 21. The objective lens 21 focuses transmitted light that has passed through the specimens X from top to bottom as a result of the illumination light coming from the LED light source 19 being radiated onto the specimens X from thereabove, and that enters the housing 5 by passing through the top plate 5a from top to bottom.

The controller 13 automatically controls the exposure time and the gain of the camera 23. In addition, the controller 13 is capable of causing the display portion 15 to display the image acquired by the camera 23 and to save that image.

In addition, the controller 13 is capable of removing brightness unevenness and emphasizing contrast by processing the image. By doing so, it is possible to enhance the visibility of the specimens X. In addition, the controller 13 is capable of counting the number of the specimens X by analyzing the image. By doing so, it is possible to perform quantitative analysis of the specimens X.

The display portion 15 is, for example, a monitor such as a liquid-crystal monitor. By employing a monitor such as a liquid-crystal monitor, it is possible to display the image of the specimens X with good image quality. This display portion 15 is, for example, disposed in a wall of the clean bench 25 so as to directly face the user with the observation apparatus 1 interposed therebetween, as shown in FIG. 1.

The foot pedal 17 is, for example, a foot switch that the user operates with his/her foot. The user can operate the foot pedal 17 while performing other work with his/her hands, and thus, it is possible to enhance work efficiency. The electromagnets 5c of the housing 5 are powered on via the controller 13 as a result of the user stepping on the foot pedal 17 once, and the electromagnets 5c are powered off via the controller 13 as a result of the user stepping on the foot pedal 17 again in the state in which the electromagnets 5c are powered on. A switch other than the foot pedal may be employed.

The operation of the observation apparatus 1, thus configured, will now be described.

In order to collect transparent specimens X such as cells by employing the observation apparatus 1 according to this embodiment while performing observation thereof, first, after accommodating the specimens X in the container 3 and allowing the specimens X to adhere to the bottom surface 3b, the lid 3a is closed, and the container 3 is fitted to the through-hole 7a of the adaptor 7 and is secured to the adaptor 7 with the screw. Then, the container 3 is placed on the top plate 5a of the housing 5 together with the adaptor 7 so that the bottom surface 3b is placed on the bottom side.

Next, illumination light is generated by activating the LED light source 19. As shown in FIG. 2, the illumination light emitted from the LED light source 19 passes through, from outside the objective lens 21 in the radial direction, the top plate 5a of the housing 5 and the bottom surface 3b of the container 3 upward from therebelow, is reflected at the inner surface of the lid 3a of the container 3, and is radiated onto the specimens X from diagonally thereabove.

Of the illumination light radiated onto the specimens X, the illumination light that has passed through the specimens X passes through the bottom surface 3b of the container 3 and the top plate 5a of the housing 5 downward from therebelow, and enters the objective lens 21 in the housing 5. At this time, the illumination light is refracted and scattered due to the shape and the refractive index of the specimens X or is dimmed due to the transmittance of the specimens X, is consequently converted to the transmitted light carrying the information about the specimens X, is focused by the objective lens 21, and is captured by the camera 23. The image of the specimens X acquired by the camera 23 is sent to and displayed on the display portion 15.

Figure 3A:
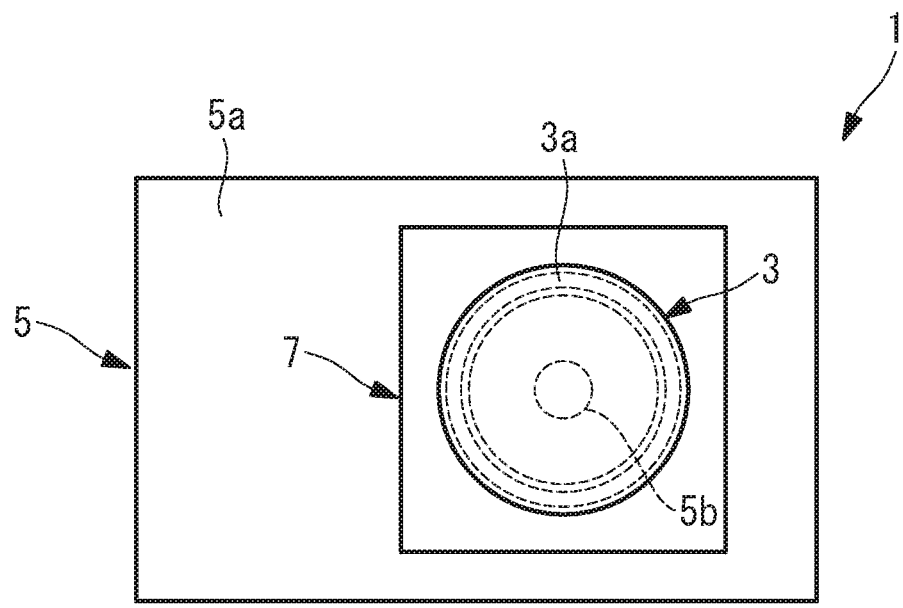
FIG. 3A is a plan view in which the observation apparatus when performing observation of a specimen is viewed from above.
Figure 3B:
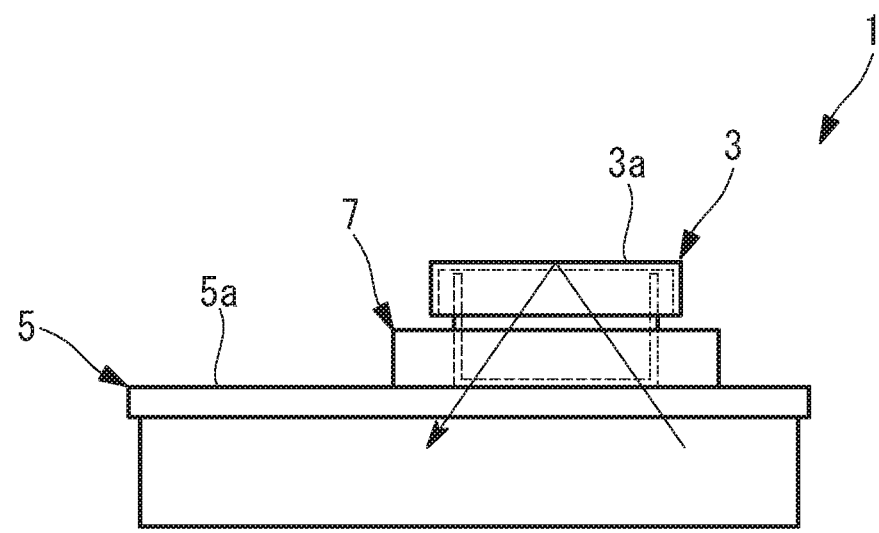
FIG. 3B is a plan view in which the observation apparatus in FIG. 3A is viewed in a direction along a top plate of a housing.

As shown in FIGS. 3A and 3B, the user grips the adaptor 7 in his/her hand, moves the container 3 on the top plate 5a with the electromagnets 5c powered off, and positions the desired specimen X (colony of cells) in the container 3 in the circle, which is the mark 5b, provided on the top plate 5a. Because the mark 5b specifies the viewing-field area of the image-acquisition portion 11, the colony of cells, which is the specimen X to be collected, is brought into the observation viewing field as a result of moving the desired specimen X together with the container 3 to the position of the circle, which is the mark 5b.

Figure 4A:
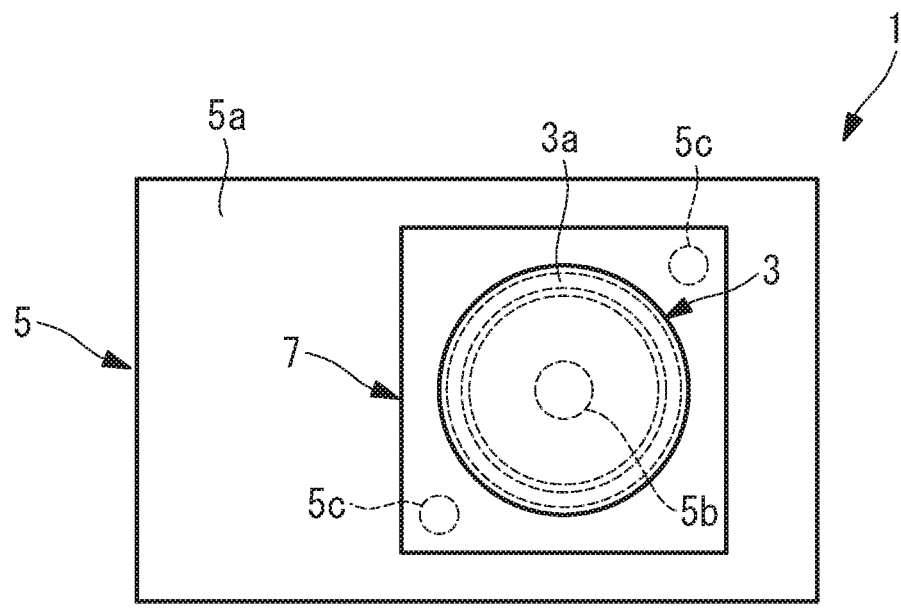
FIG. 4A is a plan view in which the observation apparatus in a state in which movement of a container is restricted by means of an electromagnet is viewed from above.
Figure 4B:
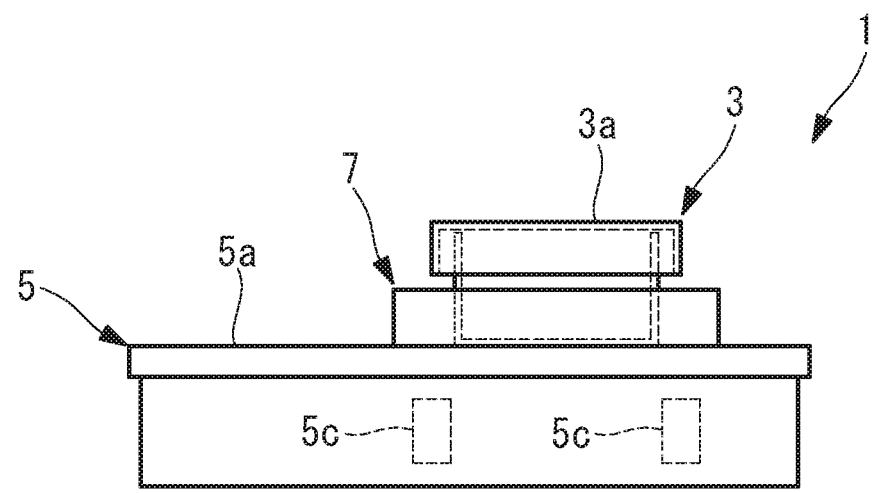
FIG. 4B is a plan view in which the observation apparatus in FIG. 4A is viewed in the direction along the top plate of the housing.
Figure 5A:
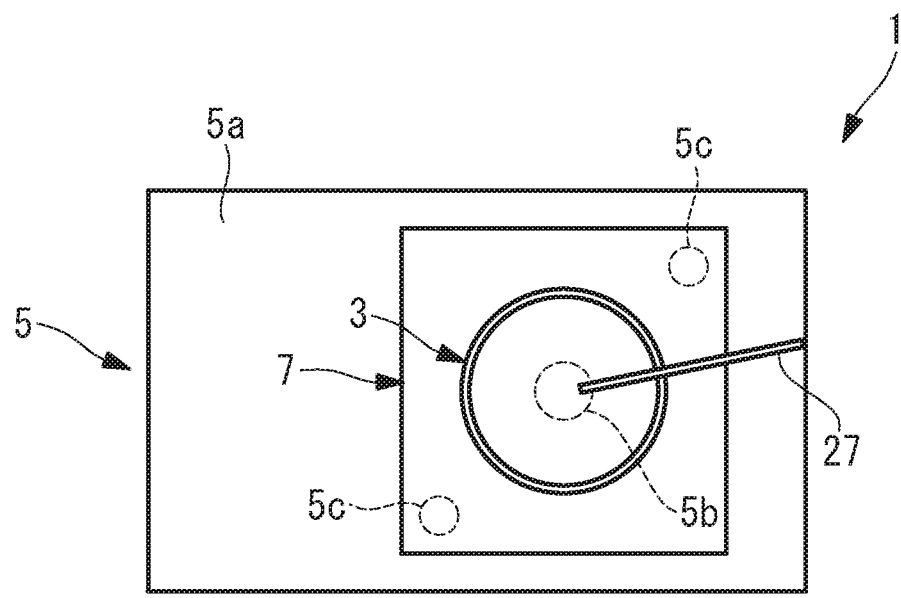
FIG. 5A is a plan view in which the observation apparatus when collecting a specimen is viewed from above.
Figure 5B:
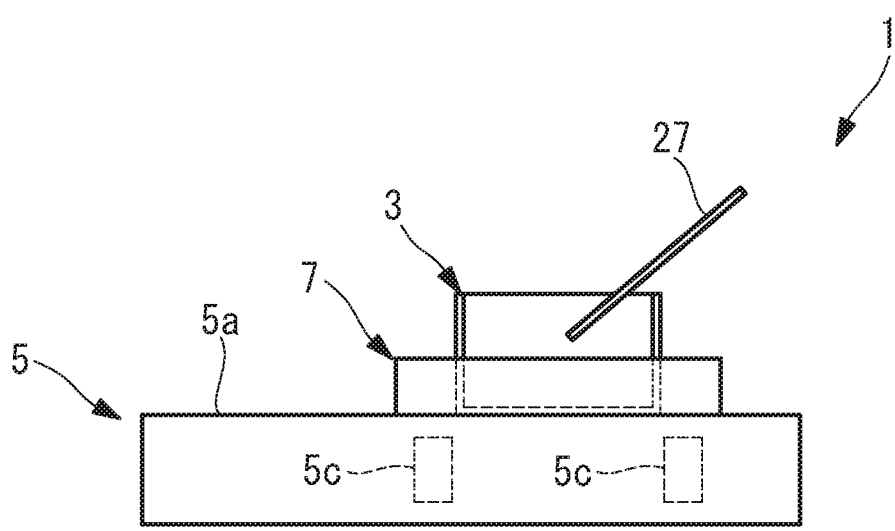
FIG. 5B is a plan view in which the observation apparatus in FIG. 5A is viewed in the direction along the top plate of the housing.

Next, the user steps on the foot pedal 1 and powers on the electromagnets 5c in the housing 5, and, as shown in FIGS. 4A and 4B, secures, together with the adaptor 7, the container 3 on the top plate 5a in the positioned state. In this state, as shown in FIGS. 5A and 5B, the user removes the lid 3a of the container 3, collects the desired specimen X from the container 3 with an aspirator 27 by using the mark 5b as an indicator, and transfers the specimen X to another container.

In this case, because the electromagnets 5c restrict the movement of the adaptor 7, which is formed of a magnetic body, even if the user is not gripping the container 3, it is possible to prevent the mark 5b from being displaced from the desired specimen X by preventing the container 3 from moving on the top plate 5a.

Once the desired specimen X has been collected, the user closes the lid 3a of the container 3, powers off the electromagnet 5c by stepping on the foot pedal 17, and the positioned state of the container 3 on the top plate 5a is cancelled.

The work in FIGS. 3A and 3B to FIGS. 5A and 5B will also be repeated for the specimen X to be collected next.

As has been described above, with the observation apparatus 1 according to this embodiment, as a result of positioning the specimens X, which are observation subjects, in the container 3, which is an observation subject, with respect to the mark 5b that is provided in the top plate 5a and that specifies the viewing-field area of the image-acquisition portion 11, it is possible to collect, while performing observation, the desired colony of cells, which is the specimen X, by distinguishing said colony from colonies in the surrounding area.

In this case, because the mark 5b is provided in advance in the top plate 5a to be placed on the container 3, the user merely needs to move the container 3 in accordance with the position of the mark 5b, and the user does not need to provide mark 5b on each container 3 while performing observation in the clean bench 25. Therefore, even in the case of using the observation apparatus in the limited space of the clean bench 25, the bothersomeness of having to provide the mark 5b that specifies the desired specimen X is eliminated, and thus, it is possible to enhance the work efficiency.

In addition, because the light-source portion 9 and the image-acquisition portion 11 are disposed below the specimens X, as compared with a transmitted-light observation apparatus in which the light-source portion and the image-acquisition portion are conventionally disposed on either side of the specimens, it is possible to make the housing 5 thin by placing the light-source portion 9 and the image-acquisition portion 11 only on one side of the specimens X. Therefore, even in the case of using the observation apparatus in a limited space of the clean bench 25, it is possible to prevent the observation apparatus 1 from interfering with the work.

It is possible to modify this embodiment as below.

As a first modification, the adaptor 7 may have, instead of the through-hole 7a, a depression (not shown) that has a bottom surface (mounting surface) on which the container 3 is placed and that is at least partially formed of an optically transparent material.

In this case, the transmitted light that has passed through and that has reached below the specimens X as a result of the illumination light being radiated from thereabove passes through the bottom surface of the depression of the adaptor 7 and is focused by the objective lens 21; therefore, it is possible to prevent the adaptor 7 from hindering the capturing of the transmitted light by the image-acquisition portion 11.

Figure 6:
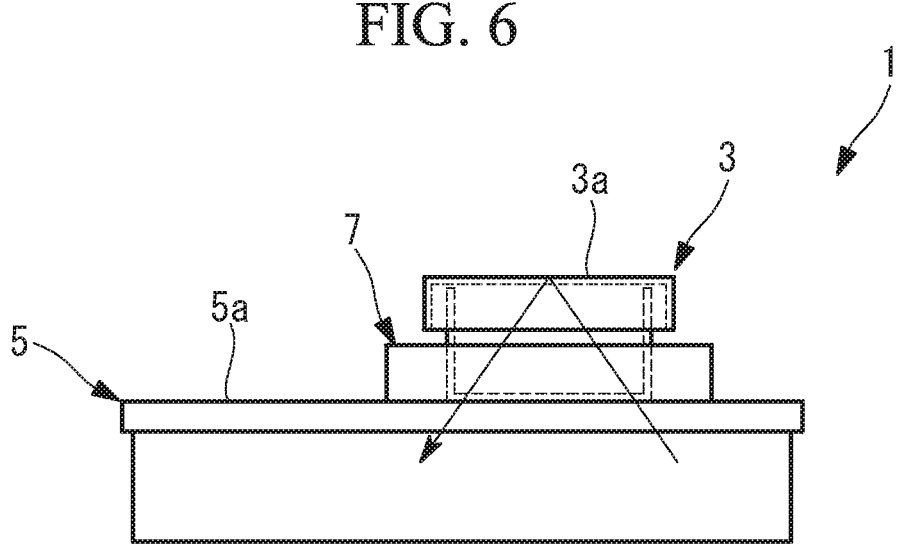
FIG. 6 is a diagram showing, in an observation apparatus according to a second modification of the first embodiment of the present invention, a manner in which a container is secured, by means of the weight of the adaptor itself, in a state in which the position of the container is set when observing a specimen.
Figure 7:
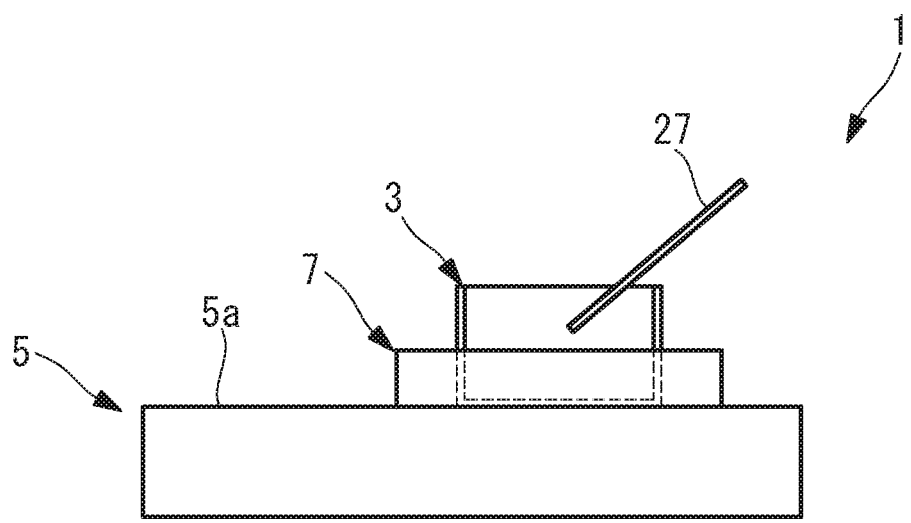
FIG. 7 is a diagram showing, in the observation apparatus according to the second modification of the first embodiment of the present invention, a manner in which the container is secured, by means of the weight of the adaptor itself, in a state in which the position of the container is set when collecting the specimen.

As a second modification, as shown in FIGS. 6 and 7, the container 3 may be secured on the top plate 5a in the positioned state by means of the weight of the adaptor 7 itself. In this case, the adaptor 7 may have a high enough weight to prevent the position of the container 3 on the top plate 5a from being displaced when performing work to remove the lid 3a from the container 3.

By doing so, even if relative movement between the container 3 and the top plate 5a is not restricted by the electromagnets 5c, it is possible to prevent the desired specimen X from being displaced from the mark 5b as a result of the container 3 being moved when removing the lid 3a from the container 3. Accordingly, for example, while the user is holding the aspirator 27 with his/her dominant hand, he/she can remove the lid 3a of the container 3 with the other hand, and it is possible to enhance work efficiency with a simple configuration.

As a third modification, the container 3 may be secured on the top plate 5a in the positioned state as a result of the user continuing to grip the adaptor 7. In this case, for example, the user may perform work with his/her dominant hand by alternatingly holding the aspirator 27 and the lid 3a of the container 3 while gripping the container 3 with his/her non-dominant hand.

By doing so, it is not necessary to restrict the relative movement between the container 3 and the top plate 5a by means of the electromagnets 5c, and, in addition, although the procedure becomes more time consuming for the user as compared with the case in which the container 3 is secured in the positioned state by means of only the weight of the adaptor 7 itself, it is possible to reliably prevent the specimens X from being displaced from the mark 5*b* as a result of the container 3 being moved when removing the lid 3*a* from the container 3.

Figure 8:
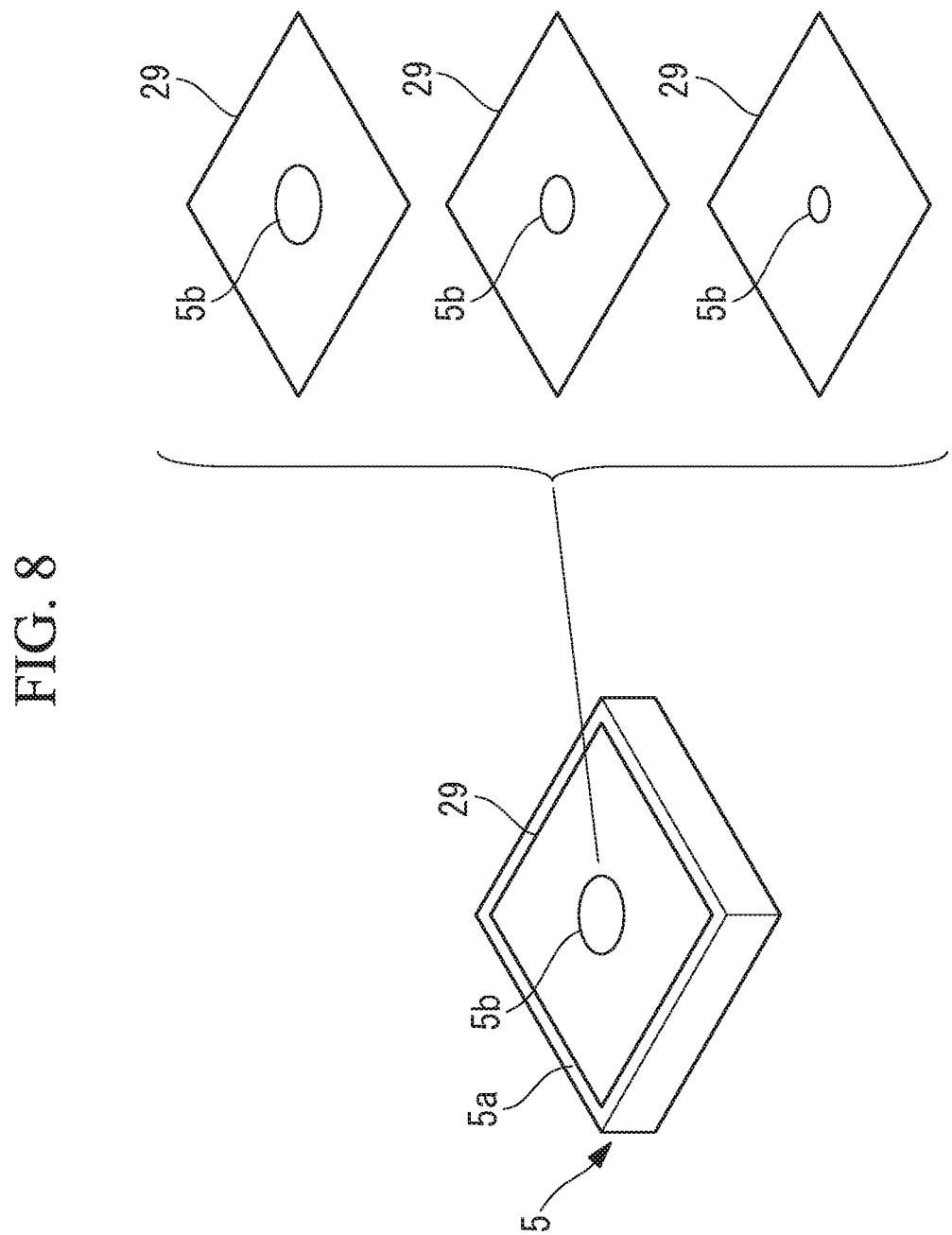
FIG. 8 is a diagram showing an example of a resin sheet employed in an observation apparatus according to a fourth modification of the first embodiment of the present invention.

As a fourth modification, as shown in FIG. 8, an attachable/detachable transparent resin sheet (sheet member) 29 may be employed in one surface of the top plate 5*a* and the mark 5*b* may be provided on this resin sheet 29 in advance instead of providing the mark 5*b* on the top plate 5*a* itself. By doing so, it is possible to provide the mark 5*b* on the top plate 5*a* with a simple configuration in which the resin sheet 29 is merely disposed on the top plate 5*a*.

In this case, a transparent adsorption layer may be provided in a surface of the resin sheet 29 that comes into contact with the top plate 5*a*. By doing so, it is possible to prevent the resin sheet 29 from being displaced on the top plate 5*a*. In addition, as shown in FIG. 8, a plurality of resin sheets 29 having the marks 5*b* of different sizes may be prepared. By doing so, it is possible to reliably distinguish the desired specimen X from other specimens X and to facilitate focusing on the desired specimen X by changing the resin sheets 29 in accordance with the size of the specimen X to be focused on.

Second Embodiment

Next, an observation apparatus according to a second embodiment of the present invention will be will be described below with reference to the drawings.

Figure 9:
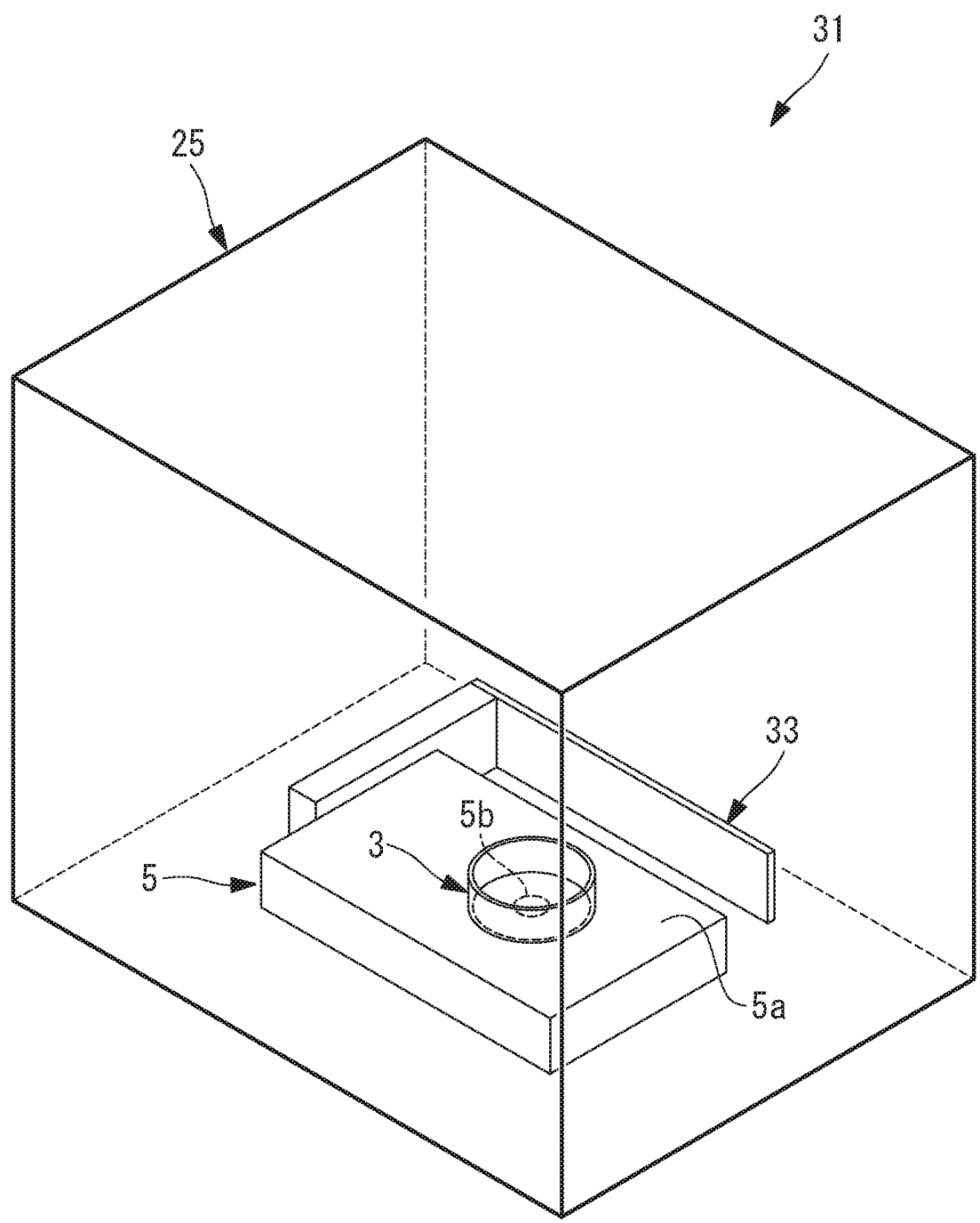
FIG. 9 is a diagram showing a state in which a reflecting member of an observation apparatus according to a second embodiment of the present invention is retracted from above the container.
Figure 10:
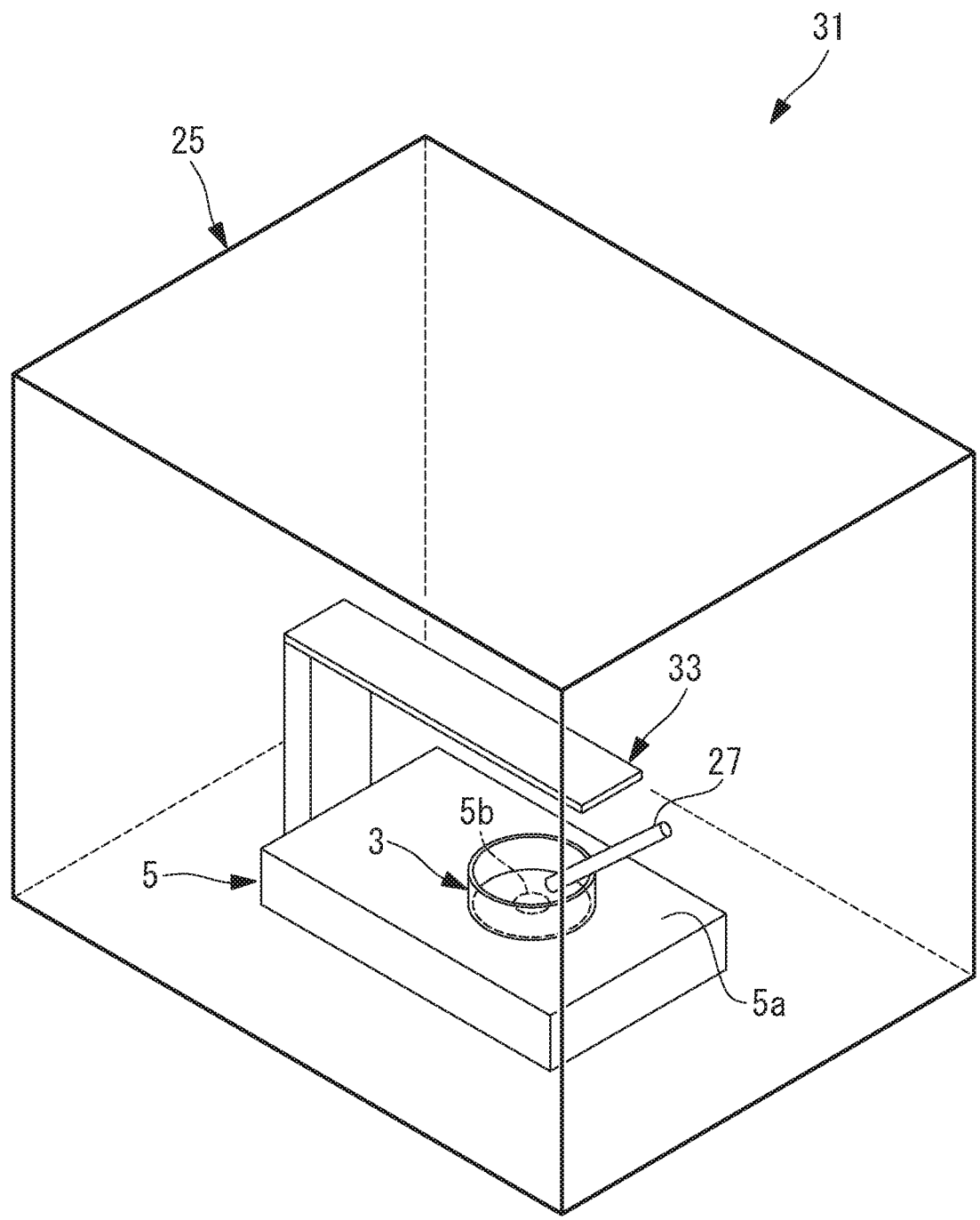
FIG. 10 is a diagram showing a state in which the reflecting member of the observation apparatus according to the second embodiment of the present invention is disposed above the container.

An observation apparatus 31 according to this embodiment and the observation apparatus 1 according to the first embodiment differ from each other in that, as shown in FIGS. 9 and 10, the observation apparatus 31 is not provided with the adaptor 7 and the electromagnet 5*c* and is provided with a reflecting member 33 that is disposed above the container 3 instead of those components.

In describing this embodiment, portions having the same configuration as those of the observation apparatus 1 according to the above-described first embodiment will be given the same reference signs, and the descriptions thereof will be omitted.

As shown in FIG. 10, the reflecting member 33 is disposed facing the top plate 5*a* so as to cover the top plate 5*a*, and reflects, toward the specimens X in the container 3, the illumination light coming from the light-source portion 9 and having passed through the top plate 5*a* and the bottom surface 3*b* of the container 3 upward from therebelow. As the reflecting member 33, for example, a glass, a resin, a mirror, or the like is employed.

In addition, as shown in FIG. 9, the reflecting member 33 is capable of being retracted from above the container 3. The reflecting member 33 is disposed above the container 3 when performing observation/collection whereas the reflecting member 33 is retracted from above the container 3 after performing observation/collection, and whereby, it is possible to prevent the reflecting member 33 from hindering work in the case in which the top plate 5*a* of the housing 5 is used as a worktable.

The operation of the observation apparatus 31, thus configured, will now be described.

In order to collect transparent specimens X such as cells by employing the observation apparatus 31 according to this embodiment while performing observation thereof, first, in the state in which the reflecting member 33 is retracted from above the top plate 5*a* of the housing 5, as shown in FIG. 9, the container 3 in which the specimens X are accommodated is placed on the top plate 5*a* of the housing 5. Then, as shown in FIG. 10, the reflecting member 33 is placed above the container 3, the lid 3*a* of the container 3 is removed, and the illumination light is generated from the LED light source 19. In this embodiment, the specimens X are observed with the lid 3*a* of the container 3 removed.

Figure 11:
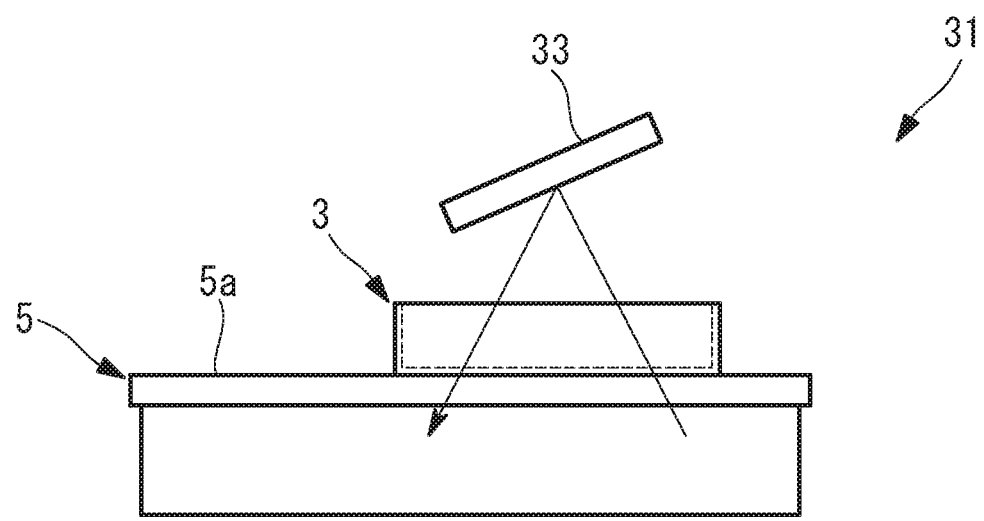
FIG. 11 is a plan view in which the observation apparatus in the state in which the reflecting member is disposed above the container is viewed in the direction along the top plate of the housing.

As shown in FIG. 11, the illumination light emitted from the LED light source 19 is, after passing through the top plate 5*a* of the housing 5 and the bottom surface 3*b* of the container 3 upward from therebelow, reflected at the reflecting member 33, and is radiated onto the specimens X from diagonally thereabove. The transmitted light that has passed through the specimens X passes through the bottom surface 3*b* of the container 3 and the top plate 5*a* of the housing 5 downward from thereabove, enters the housing 5, is focused by the objective lens 21, and is captured by the camera 23.

The user grips the container 3 with his/her hand and moves the container 3 on the top plate 5*a*, and positions the desired specimen X (colony of cells) in the container 3 in the circle, which is the mark 5*b*, provided on the top plate 5*a*. By doing so, the colony of cells, which is the specimen X to be collected, is brought into the viewing field.

Next, the user grips the aspirator 27 with his/her dominant hand, for example, while gripping the container 3 with the opposite hand from the dominant hand, collects, by means of the aspirator 27, the desired specimen X from the container 3 by using the mark 5*b* as the indicator, and transfers the specimen X to another container.

Similarly, regarding the specimen X to be collected next, the container 3 is moved by hand and positioned in the circle, which is the mark 5*b*, while the container 3 is gripped with one of the hands, the aspirator 27 is gripped with the other hand, and the specimen X is collected from the container 3 by using the mark 5*b*. Once all of the desired specimens X are collected in this way, the reflecting member 33 is retracted from above the container 3, as shown in FIG. 9.

With the observation apparatus 31 according to this embodiment, as a result of irradiating the specimens X with the illumination light coming from the LED light source 19 being reflected by the reflecting member 33 instead of the lid 3*a* of the container 3, the illumination conditions do not change depending on the type of the container 3, and thus, it is possible to stabilize the image quality. In addition, because it is not necessary to close the lid 3*a* of the container 3 when performing observation, it is possible to avoid displacement of the position of the container 3 caused by opening the lid 3*a* when collecting the specimen X. Therefore, there is no concern that the desired specimen X will be displaced from the mark 5*b* due to movement of the container 3 even if the adaptor 7 and the electromagnet 5*c* are not provided, and thus, it is possible to simplify the configuration. Note that, in order to more reliably prevent the movement of the container 3, the adaptor 7 and the electromagnet 5*c* may be employed.

It is possible to modify this embodiment as follows.

Although the reflecting member 33 is employed in this embodiment, in the case in which the specimens X are accommodated in a container that does not have the lid 3*a*, such as a petri dish (no lid), the container 3 may be filled with a solution (for example, a culturing medium, a phosphate buffer, or the like), the specimens X may be immersed in the solution, and the illumination that has passed through the bottom surface 3*b* upward from therebelow may be reflected by a liquid surface at the top of the solution. In the case in which the specimens X are accommodated in the container 3 having the lid 3*a* also, the container 3 may be filled with a solution (for example, a culturing medium, a phosphate buffer, or the like) and the specimens X may be immersed in the solution.

Figure 12:
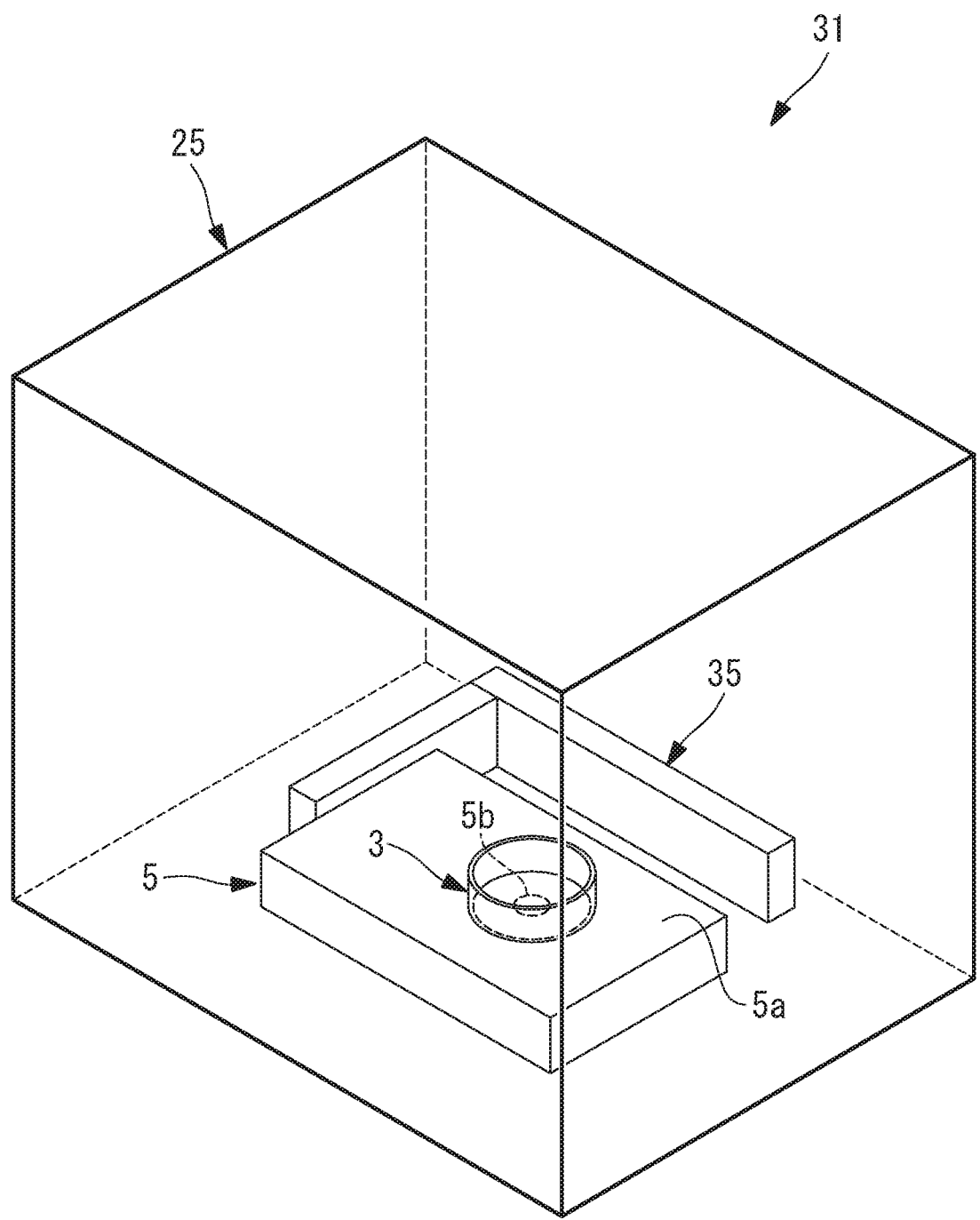
FIG. 12 is a diagram showing a state in which another light-source portion of an observation apparatus according to a modification of the second embodiment of the present invention is retracted from above the container.
Figure 13:
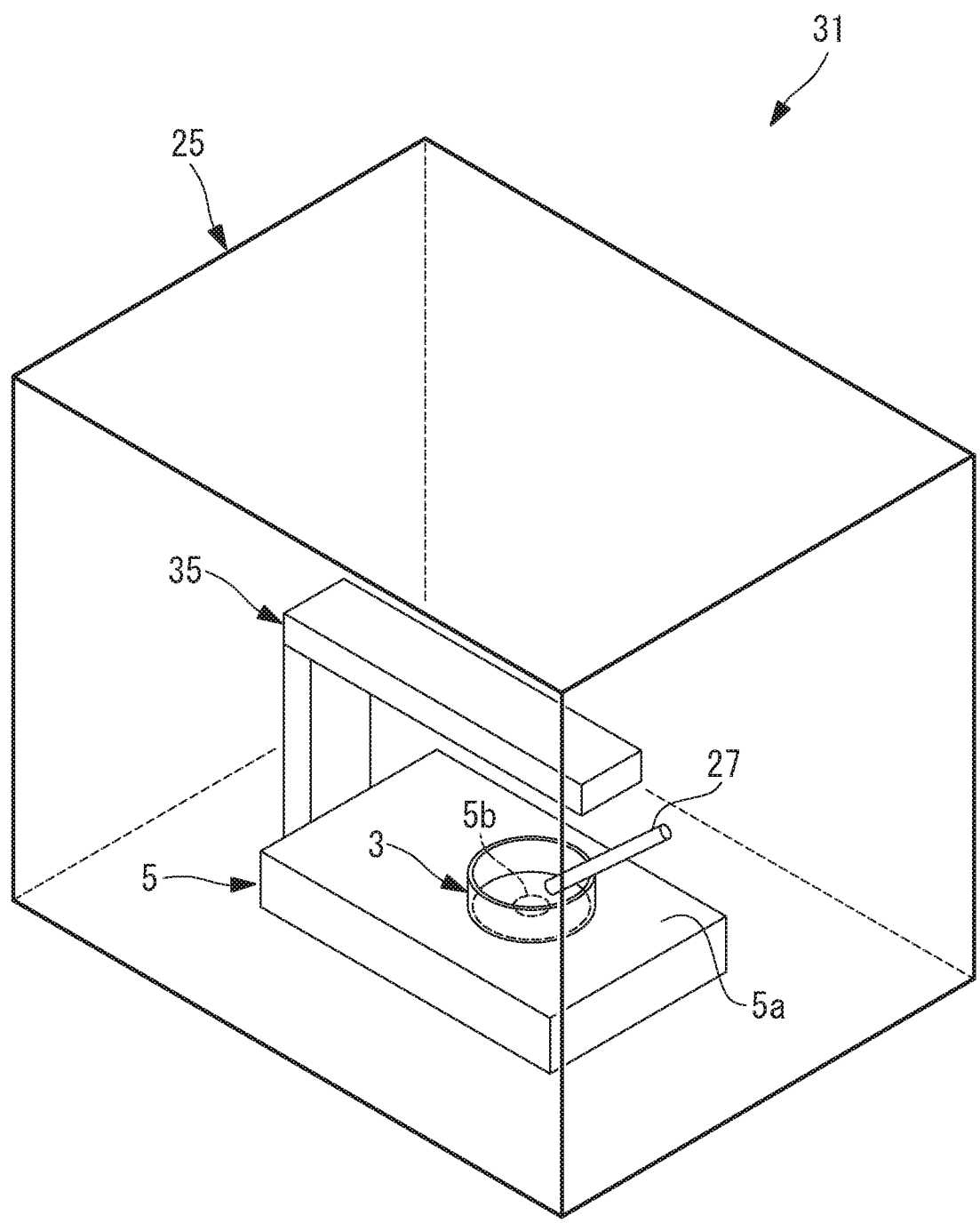
FIG. 13 is a diagram showing a state in which the other light-source portion according to the modification of the second embodiment of the present invention is disposed above the container.

In addition, for example, as shown in FIGS. 12 and 13, another light-source portion 35 that emits illumination light toward an area below the specimens X from thereabove may be additionally provided, and transmitted light that is emitted from the other light-source portion 35, that has passed through the specimen X and the top plate 5a, and that has entered the housing 5 may be captured by the camera 23. As shown in FIG. 12, the other light-source portion 35 may be capable of being retracted from above the container 3.

In this case, when performing observation, the container 3 is moved with one hand and the specimen X is positioned in the circle, which serves as the mark 5b, and, when performing collection, as shown in FIG. 13, the container 3 continues to be gripped with the same hand, the aspirator 27 is gripped with the other hand, and the desired specimen X may be collected from the container 3 by using the mark 5b as the indicator.

With this modification, in the case in which the specimens X are observed by using the illumination light coming from the other light-source portion 35, the lid 3a of the container 3 or the reflecting member 33 for reflecting the illumination light above the specimens X is not necessary. In addition, as a result of retracting the other light-source portion 35 from above the container 3 after performing observation/collection, it is possible to prevent the other light-source portion 35 from hindering work.

It is possible to modify the individual embodiments described above as below.

For example, the light-source portion 9 may be provided with a diffusion plate (not shown) that spreads out the illumination light emitted from the LED light source 19. By doing so, because the illumination light emitted from the LED light source 19 is evenly spread out by the diffusion plate, it is possible to irradiate the specimen X with illumination light having an even intensity with low illumination irregularity.

In addition, in the individual embodiments described above, the light-source portion 9 is provided with the single LED light source 19; however, alternatively, the light-source portion may be provided with a plurality of LED light sources 19 that are disposed in the area surrounding the objective lens 21 with spacings therebetween in a circumferential direction.

By turning on only the LED light sources 19 at specific positions in the circumferential direction of the objective lens 21, it is possible to illuminate the specimens X only from specific directions in the circumferential direction. In addition, by simultaneously turning on the LED light sources 19 that are disposed in two or more directions in the circumferential direction of the objective lens 21, in particular, directions that are axisymmetric with respect to the optical axis of the objective lens 21, it is possible to irradiate the specimens X with illumination light in which the illumination irregularity is reduced.

In this modification, the plurality of LED light sources 19 may be disposed not only in the circumferential direction of the objective lens 21 but also in a redial direction of the objective lens 21 with spacings therebetween. In this case, specific LED light sources 19 may independently be turned on. For example, by turning on only the LED light sources 19 that are at different positions in the radial direction of the objective lens 2, it is possible to change the angle of the illumination light that is radiated onto the specimens X from diagonally thereabove.

Figure 14:
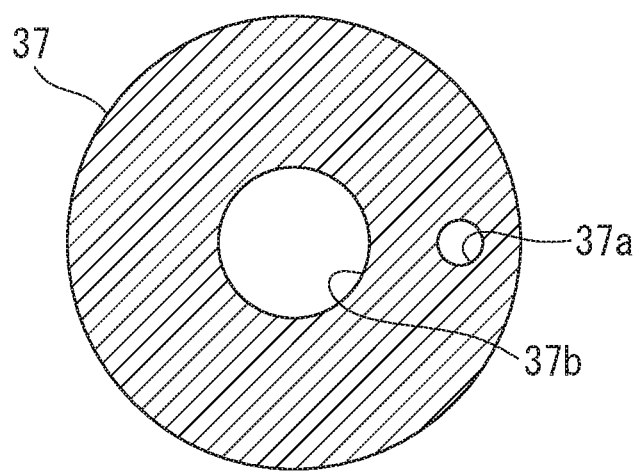
FIG. 14 is a plan view showing an example of a light-blocking member having a single circular opening.

In the above-described modification, the illumination light is emitted by switching among the plurality of LED light sources 19; however, alternatively, as shown in FIG. 14, a light-blocking member 37 that blocks the illumination light coming from the LED light sources 19 may be employed and disposed above the LED light sources 19.

As shown FIG. 14, the light-blocking member 37 is provided with an opening 37a formed in a portion in the circumferential direction or a portion in the radial direction and a transmission hole 37b that allows the transmitted light, which has passed through the specimens X after being reflected at the inner surface of the lid 3a of the container 3, to pass therethrough. By switching among a plurality of light-blocking members 37 having the transmission holes 37b at different positions, it is possible to change the irradiation angle and the irradiation direction of the illumination light in accordance with the position of the opening 37a in each light-blocking member 37.

In this case, although the plurality of LED light sources 19 may be employed as the light-source portion 9 as with the first modification, the function for changing the positions at which the illumination light is emitted is not necessary, and a unit provided with an arbitrary light source may be employed so long as the light source is capable of emitting the illumination light from an area that is larger than that of the opening 37a.

FIG. 14 shows the light-blocking member 37 having the circular opening 37a as an example; however, alternatively, a member in which the size, the position, the shape, and the number of the openings 37a are arbitrary, for example, a fan-shaped opening 37a, an annular opening 37a, or the like, may be employed.

As has been described above, although the embodiments of the present invention have been described in detail with reference to the drawings, specific configurations are not limited to these embodiments, and design alterations or the like within a range that does not depart from the scope of the present invention are also encompassed. For example, the present invention is not limited to the forms in which the present invention is applied to the above-described individual embodiments and modifications, the present invention may be applied to embodiments in which these embodiments and modifications are combined, as appropriate, and it is not particularly limited.

As a result, the above-described embodiments also lead to the following aspects.

An aspect of the present invention is an observation apparatus including: a top plate on which a container in which specimen is accommodated can be placed, and through which illumination light can pass; and an image-acquisition portion that captures, below the specimen and the top plate, transmitted light, which is the illumination light that has passed through the specimen from thereabove and that has passed through the top plate, wherein the top plate is provided with a mark that specifies a viewing-field area of the image-acquisition portion.

With this aspect, when the illumination light is radiated, from above, onto the specimen in the container placed on the top plate, the transmitted light that has passed through the specimen and that has passed through the top plate is captured by the image-acquisition portion below the specimen. In this case, by positioning the specimen in the container, which serves as the observation subject, with respect to the mark that is provided on the top plate and that specifies the viewing-field area of the image-acquisition portion, it is possible to collect a desired specimen while performing observation by distinguishing the desired specimen from specimens in the surrounding area.

Because this mark is provided in advance on the top plate on which the container is placed, a user merely needs to move the container in accordance with the position of the mark, and the user does not need to provide the mark on each container. Therefore, the bothersomeness of having to provide the mark for specifying a desired specimen is eliminated, and it is possible to enhance work efficiency, even when using the observation apparatus in a limited space such as a clean bench.

In the above-described aspect, the mark may be provided on the top plate itself.

By employing such a configuration, it is possible to reduce the number of components.

In the above-described aspect, an attachable/detachable sheet member is provided on one surface of the top plate, and the mark may be provided on the sheet member.

By employing such a configuration, it is possible to provide the mark on the top plate with a simple configuration in which the sheet member is merely disposed on the top plate.

The above-described aspect may be provided with a plurality of the sheet members each having the mark of different size.

By employing such a configuration, by changing the sheet member in accordance with the size of a specimen to be focused on, it is possible to facilitate to focus on the desired specimen by reliably distinguishing the desired specimen from other specimens.

The above-described aspect may be provided with an adaptor that is placed on the top plate and that holds the container.

By employing such a configuration, by securing the adaptor by means of gripping or the like, the user can prevent the container from being moved while performing work, and he/she can prevent the mark from being displaced from the specimen he/she is focusing on.

In the above-described aspect, the adaptor may have a mounting surface on which the container is placed, and that is at least partially formed of an optically transparent material.

By employing such a configuration, the transmitted light that has passed through the specimen passes through the mounting surface of the adaptor and is captured by the image-acquisition portion. Therefore, it is possible to prevent the adaptor from hindering capturing of the transmitted light by the image-acquisition portion.

In the above-described aspect, the adaptor may have a through-hole for allowing the transmitted light to pass therethrough.

By employing such a configuration, the transmitted light that has passed through the specimen passes through the through-hole of the adaptor and is captured by the image-acquisition portion. Therefore, it is possible to prevent the adaptor from hindering capturing of the transmitted light by the image-acquisition portion.

The above-described aspect may be provided with a movement restricting portion that restricts relative movement between the adaptor and the top plate.

By employing such a configuration, with the movement restricting portion, it is possible to prevent the container from being moved without the user having to grip the adaptor, and it is possible to further enhance the work efficiency.

In the above-described aspect, the movement restricting portion may be an electromagnet that, as a result of being powered on, restricts relative movement between the adaptor and the top plate, and that, as a result of being powered off, cancels the restriction on the relative movement between the adaptor and the top plate.

By employing such a configuration, it is possible to restrict the relative movement between the adaptor and the top plate and to cancel the restriction by means of a simple configuration in which the electromagnet is merely powered on and off.

The above-described aspect may be provided with a light-source portion that emits the illumination light toward an area above the specimen from therebelow, wherein the image-acquisition portion may capture the transmitted light that has passed through the specimen and the top plate as a result of the illumination light emitted from the light-source portion being reflected above the specimen.

By employing such a configuration, as a result of disposing both the light-source portion and the image-acquisition portion below the specimen, the height of the apparatus can be kept low as compared with the case in which the light-source portion and the image-acquisition portion are disposed on either side of the specimen such that the two components are separated above and below the specimen. By doing so, it is possible to achieve work-efficiency enhancement by preventing interference with work when using the observation apparatus in a limited space such as a clean bench.

In the above-described aspect, the image-acquisition portion may be provided with an objective lens that focuses the transmitted light that has passed through the specimen, and the light-source portion may emit the illumination light above the specimen from outside the objective lens in a radial direction.

By employing such a configuration, the transmitted light that has passed through the specimen is captured by the image-acquisition portion, the transmitted light being the illumination light that is emitted upward from the specimen from the light-source portion disposed outside the objective lens, which is disposed below the specimen, in the radial direction and that is reflected above the specimen and made incident on the specimen from diagonally above with respect to the optical axis of the objective lens. By appropriately setting the incidence angle with respect to the specimen, it is possible to form contrast in the image of the specimen, and it is possible to acquire an image with high visibility even with a transparent imaging subject such as cells.

In the above-described aspect, the light-source portion may be capable of independently emitting the illumination light from different positions in radial directions of the objective lens.

By doing so, as a result of causing the illumination light to be emitted from a different radial-direction position of the light-source portion, it is possible to change the angle at which the reflected light, which has been reflected by the same reflection surface disposed above the specimen, is made incident on the specimen. In other words, the reflected light of the illumination light that is emitted from a position close to the objective lens in the radial direction is made incident on the specimen at a small angle with respect to the optical axis, whereas the reflected light of the illumination light that is emitted from a position far from the objective lens in the radial direction is made incident on the specimen at a large angle with respect to the optical axis.

Accordingly, it is possible to use bright-field illumination in which the illumination irregularity is low in the case in which the incidence angle is smaller than the acceptance angle of the objective lens, in addition, it is possible to use dark-field illumination with which a fine structure is emphasized in the case in which the incidence angle is greater than the acceptance angle of the objective lens, and, furthermore, it is possible to use oblique illumination with which it is possible to three-dimensionally view the specimen in the case in which the incidence angle is equivalent to the acceptance angle of the objective lens.

In the above-described aspect, the light-source portion may be capable of simultaneously emitting the illumination light from different positions in circumferential directions of the objective lens.

By doing so, the illumination light is simultaneously emitted from a plurality of positions in the circumferential directions of the objective lens, and it is possible to reduce the illumination irregularity.

In the above-described aspect, the light-source portion may be provided with a plurality of light sources that are arrayed in an area surrounding the objective lens and that are capable of independently being turned on.

By employing such a configuration, it is possible to determine the circumferential-direction position of the illumination light by turning on one of the plurality of light sources. Also, by changing the circumferential-direction position of the light source to be turned on, it is possible to capture images of the specimen that are illuminated from different directions. In particular, in images captured by using the above-described oblique illumination, it is possible to capture images in which shadows are formed in different ways.

In the above-described aspect, the light-source portion may be provided with a light source that is disposed below the specimen, and a light-blocking member that has an opening that allows, of illumination light coming from the light source, only the illumination light in a specific radial-direction position to pass therethrough.

By employing such a configuration, the illumination light coming from the light source is blocked by the light-blocking member, and only the illumination light that passes through the opening is reflected above the specimen and made incident on the specimen. Therefore, by adjusting the position of the opening of the light-blocking member, it is possible to change the direction or the angle at which the reflected light is made incident on the specimen without having to change the position at which the light source is turned on.

In the above-described aspect, the light-source portion is provided with a diffusion plate that spreads out the illumination light.

By employing such a configuration, it is possible to irradiate the specimen with the illumination light that is evenly spread out by the diffusion plate.

The above-described aspect may be provided with a reflecting member that is disposed above the container and that reflects the illumination light coming from the light-source portion.

By employing such a configuration, it is possible to reflect the illumination light coming from the light-source portion above the specimen by means of the reflecting member even if the container does not have a lid. Therefore, the time-consuming procedure of removing the lid from the container is eliminated when collecting the specimen from the container after performing observation.

In the above-described aspect, the reflecting member may be capable of being retracted from above the container.

By employing such a configuration, by retracting the reflecting member from above the container after performing observation, it is possible to prevent the reflecting member from hindering work.

In the above-described aspect, another light-source portion that emits the illumination light toward an area below the specimen from thereabove may be provided, and the image-acquisition portion may capture the transmitted light, which is the illumination light that has been emitted from the other light-source portion and that has passed through the specimen and the top plate.

By employing such a configuration, it is possible to observe the specimen by using the transmitted light, which is formed from the illumination light radiated onto the specimen from thereabove from the other light-source portion. Therefore, in the case in which the specimen is observed by using the illumination light coming from the other light-source portion, a lid and a reflecting member for reflecting the illumination light above the specimen are not necessary In the above-described aspect, the other light-source portion may be capable of being retracted from above the container.

By employing such a configuration, by retracting the other light-source portion from above the container after performing observation, it is possible to prevent the other light-source portion from hindering work.

In the above-described aspect, the specimen may be accommodated in a container formed of an optically transparent material, and the illumination light may be reflected by an inner surface of a top-plate portion of the container, which is disposed above the specimen.

By employing such a configuration, by merely disposing, above the light-source portion and the image-acquisition portion, the container that accommodates the specimen in the interior thereof and that has the top-plate portion, it is possible to irradiate the specimen in the container with the illumination light emitted from the light-source portion by causing the illumination light to be reflected at the inner surface of the top-plate portion of the container.

In the above-described aspect, the specimen may be immersed in a solution, and the illumination light may be reflected by a liquid surface at the top of the solution.

By employing such a configuration, it is possible to irradiate the specimen in the container with the illumination light emitted from the light-source portion by causing illumination light to be reflected at the liquid surface of the solution even in the case in which the specimen is accommodated in a container that does not have a top-plate portion or a container in which it is not possible to provide a reflecting member.

An observation apparatus according to the present invention affords an advantage in that the bothersomeness of having to provide a mark for specifying a desired specimen is eliminated, and it is possible to enhance the work efficiency even when using the observation apparatus in a limited space such as a clean bench.

REFERENCE SIGNS LIST 1, 31 observation apparatus
3 container
3a lid (top-plate portion)
5a top plate
5b mark
5c electromagnet (movement restricting portion)
7 adaptor
7a through-hole
9 light-source portion 11 image-acquisition portion
19 LED light source (light source)
29 resin sheet (sheet member)
33 reflecting member
35 another light-source portion
37 light-blocking member
37a opening
X specimen

The invention claimed is:

1. An observation apparatus comprising:
a top plate on which a container in which a specimen is accommodated can be placed, and through which illumination light can pass;
a light source that emits the illumination light upward from below the specimen;
an objective lens that focuses, below the specimen and the top plate, transmitted light which is the illumination light that has passed through the specimen after being reflected from above the specimen and that has passed through the top plate, a position of the objective lens being fixed such that a relative positional relationship between the objective lens and the top plate remains constant; and
a camera that captures the transmitted light focused by the objective lens,
wherein:
the light source emits the illumination light toward an area above the specimen from outside the objective lens in a radial direction, and
the top plate is provided with a mark that specifies a viewing-field area of the camera.

2. The observation apparatus according to claim 1, wherein the mark is provided on the top plate itself.

3. The observation apparatus according to claim 1, wherein:
a sheet member is detachably provided on one surface of the top plate, and
the mark is provided on the sheet member.

4. The observation apparatus according to claim 3, wherein a plurality of the sheet members are provided, the marks provided on the plurality of sheet members being different from each other in size.

5. The observation apparatus according to claim 1, further comprising an adaptor that is placed on the top plate and that holds the container.

6. The observation according to claim 5, wherein the adaptor has a mounting surface on which the container is placed, the mounting surface being at least partially formed of an optically transparent material.

7. The observation apparatus according to claim 5, wherein the adaptor has a through-hole through which the transmitted light can pass.

8. The observation apparatus according to claim 5, further comprising a movement restricting portion that restricts relative movement between the adaptor and the top plate.

9. The observation apparatus according to claim 8, wherein the movement restricting portion comprises an electromagnet that, as a result of being powered on, puts a restriction on the relative movement between the adaptor and the top plate, and that, as a result of being powered off, cancels the restriction on the relative movement between the adaptor and the top plate.

10. The observation apparatus according to claim 1, wherein the light source is configured to emit the illumination light from different positions in the radial direction of the objective lens.

11. The observation apparatus according to claim 1, wherein the light source is configured to emit the illumination light from different positions in a circumferential direction of the objective lens.

12. The observation apparatus according to claim 1, wherein the light source comprises a plurality of light sources that are arrayed in an area surrounding the objective lens and that are configured to be selectively turned on.

13. The observation apparatus according to claim 1, wherein the light source comprises:
at least one light source that is disposed below the specimen; and
a light-blocking member that has an opening that allows, of illumination light emitted from the at least one light source, only illumination light in a specific radial-direction position to pass therethrough.

14. The observation apparatus according to claim 1, wherein the light source comprises a diffusion plate that spreads out the illumination light.

15. The observation apparatus according to 1, further comprising:
a reflecting member that is disposed above the container and that reflects the illumination light emitted from the light source.

16. The observation apparatus according to claim 15, wherein the reflecting member is retractably provided above the container.

17. The observation apparatus according to claim 1, further comprising:
a second light source that emits illumination light toward an area below the specimen from above the specimen,
wherein the camera further captures transmitted light which is the illumination light that is emitted from the second light source and that has passed through the specimen and the top plate.

18. The observation apparatus according to claim 17, wherein the other light source is retractably provided above the container.

19. The observation apparatus according to claim 1, wherein:
the container is formed of an optically transparent material, and
the illumination light is reflected by an inner surface of a top-plate portion of the container, which is disposed above the specimen.

20. The observation apparatus according to claim 1, wherein:
the specimen is immersed in a solution, and
the illumination light is reflected by a top liquid surface of the solution.

21. The observation apparatus according to claim 1, wherein the mark specifies a desired-specimen position in the viewing-field area of the camera.

22. The observation apparatus according to claim 1, further comprising:
a housing having the top plate,
wherein the housing accommodates the light source and the camera.

23. A method for observing a specimen accommodated in a container placed on a top plate through which illumination light can pass, the top plate being provided with a mark, and the method comprising:
emitting the illumination light upward from below the specimen;
focusing, by an objective provided below the specimen and the top plate, transmitted light which is the illumination light that has passed through the specimen after being reflected from above the specimen and that has passed through the top plate;

capturing, by a camera, an image of the transmitted light focused by the objective lens; and moving the specimen together with the container to a position of the mark to collect the specimen from the container by using the mark as an indicator, wherein the light source emits the illumination light toward an area above the specimen from a position radially outward of a position at which the transmitted light is focused.

* * * * *